(12) United States Patent
Auerbach et al.

(10) Patent No.: US 11,432,754 B2
(45) Date of Patent: Sep. 6, 2022

(54) INTRACARDIAC ELECTROCARDIOGRAM PRESENTATION

(71) Applicant: BIOSENSE WEBSTER (ISRAEL) LTD., Yokneam (IL)

(72) Inventors: Shmuel Auerbach, Kerem Maharal (IL); Stanislav Goldberg, Haifa (IL); Oded Baron, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 461 days.

(21) Appl. No.: 16/580,122

(22) Filed: Sep. 24, 2019

(65) Prior Publication Data
US 2021/0085200 A1   Mar. 25, 2021

(51) Int. Cl.
*A61B 5/339* (2021.01)
*G16H 30/20* (2018.01)
(Continued)

(52) U.S. Cl.
CPC .............. *A61B 5/339* (2021.01); *A61B 5/065* (2013.01); *A61B 5/287* (2021.01); *A61B 5/6859* (2013.01); *G06T 11/001* (2013.01); *G16H 30/20* (2018.01); *G06T 2210/41* (2013.01); *G06T 2210/62* (2013.01)

(58) Field of Classification Search
CPC ......... A61B 5/065; A61B 5/287; A61B 5/339; A61B 5/6859; A61B 5/6869; G06T 11/001; G06T 2210/41; G06T 2210/62; G16H 30/20
See application file for complete search history.

(56) References Cited

U.S. PATENT DOCUMENTS 3,599,033 A   8/1971 Stettiner
4,098,267 A   7/1978 Stein
(Continued)

FOREIGN PATENT DOCUMENTS

EP   3254618 A1   12/2017
EP   3520693 A1   8/2019
WO   WO1996005768 A1   2/1996

OTHER PUBLICATIONS

European Search Report for corresponding EPA No. 20197693.3 dated Feb. 22, 2021.

*Primary Examiner* — Jonathan T Kuo (57) ABSTRACT

In one embodiment, a medical system includes a catheter to be inserted into a chamber of a heart of a living subject, and including catheter electrodes to contact tissue at respective locations within the chamber of the heart, a display, and processing circuitry to receive signals from the catheter, and in response to the signals, sample respective voltage values of the signals at respective timing values, and render to the display respective intracardiac electrograms (IEGM) presentation strips representing electrical activity in the tissue that is sensed by the catheter electrodes at the respective locations, each of the IEGM presentation strips including a linear array of respective shapes associated with, and arranged in a temporal order of, respective ones of the timing values, fillers of the respective shapes being formatted responsively to respective ones of the sampled voltage values of a respective one of the signals sampled at respective ones of the timing values.

19 Claims, 5 Drawing Sheets

(51) Int. Cl.
*A61B 5/287* (2021.01)
*A61B 5/06* (2006.01)
*A61B 5/00* (2006.01)
*G06T 11/00* (2006.01)

(56) References Cited

U.S. PATENT DOCUMENTS

| | | |
|---|---|---|
| 4,864,516 A | 9/1989 | Gaither |
| 5,391,199 A | 2/1995 | Ben Haim |
| 5,758,181 A | 5/1998 | Becker |
| 6,239,724 B1 | 5/2001 | Doron |
| 6,332,089 B1 | 12/2001 | Acker |
| 6,484,118 B1 | 11/2002 | Govari |
| 6,611,839 B1 | 8/2003 | Nwabueze |
| 6,618,612 B1 | 9/2003 | Acker |
| 6,690,963 B2 | 2/2004 | Ben Haim |
| 6,892,093 B2 | 5/2005 | Brodnick |
| 7,389,204 B2 | 6/2008 | Eryurek |
| 7,756,576 B2 | 7/2010 | Levin |
| 7,848,787 B2 | 12/2010 | Osadchy |
| 7,869,865 B2 | 1/2011 | Govari |
| 2002/0065455 A1 | 5/2002 | Ben Haim |
| 2003/0120150 A1 | 6/2003 | Govari |
| 2004/0054294 A1* | 3/2004 | Ramseth ............... G16H 40/40 600/509 |
| 2004/0068178 A1 | 4/2004 | Govari |
| 2004/0241730 A1 | 12/2004 | Yakhini |
| 2005/0197803 A1 | 9/2005 | Eryurek |
| 2005/0206644 A1 | 9/2005 | Kincaid |
| 2011/0021936 A1* | 1/2011 | Luo ..................... A61B 5/4884 345/604 |
| 2015/0313491 A1* | 11/2015 | Edwards ............... A61B 5/243 600/509 |
| 2017/0079542 A1* | 3/2017 | Spector ................. A61B 5/316 |
| 2017/0354339 A1* | 12/2017 | Zeidan ................ A61B 5/6858 |

\* cited by examiner

INTRACARDIAC ELECTROCARDIOGRAM PRESENTATION

FIELD OF THE INVENTION

The present invention relates to medical systems, and in particular, but not exclusively to, catheter-based systems.

BACKGROUND

A wide range of medical procedures involve placing probes, such as catheters, within a patient's body. Location sensing systems have been developed for tracking such probes. Magnetic location sensing is one of the methods known in the art. In magnetic location sensing, magnetic field generators are typically placed at known locations external to the patient. A magnetic field sensor within the distal end of the probe generates electrical signals in response to these magnetic fields, which are processed to determine the coordinate locations of the distal end of the probe. These methods and systems are described in U.S. Pat. Nos. 5,391,199, 6,690,963, 6,484,118, 6,239,724, 6,618,612 and 6,332,089, in PCT International Publication No. WO 1996/005768, and in U.S. Patent Application Publications Nos. 2002/006455 and 2003/0120150 and 2004/0068178. Locations may also be tracked using impedance or current based systems.

One medical procedure in which these types of probes or catheters have proved extremely useful is in the treatment of cardiac arrhythmias. Cardiac arrhythmias and atrial fibrillation in particular, persist as common and dangerous medical ailments, especially in the aging population.

Diagnosis and treatment of cardiac arrhythmias include mapping the electrical properties of heart tissue, especially the endocardium and the heart volume, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure, mapping followed by ablation, electrical activity at points within the heart is typically sensed and measured by advancing a catheter containing one or more electrical sensors into the heart, and acquiring data at a multiplicity of points. These data are then utilized to select the endocardial target areas at which the ablation is to be performed.

Electrode catheters have been in common use in medical practice for many years. They are used to stimulate and map electrical activity in the heart and to ablate sites of aberrant electrical activity. In use, the electrode catheter is inserted into a major vein or artery, e.g., femoral artery, and then guided into the chamber of the heart of concern. A typical ablation procedure involves the insertion of a catheter having a one or more electrodes at its distal end into a heart chamber. A reference electrode may be provided, generally taped to the skin of the patient or by means of a second catheter that is positioned in or near the heart. RF (radio frequency) current is applied to the tip electrode(s) of the ablating catheter, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive.

SUMMARY

There is provided in accordance with an embodiment of the present disclosure, a medical system, including a catheter configured to be inserted into a chamber of a heart of a living subject, and including catheter electrodes configured to contact tissue at respective locations within the chamber of the heart, a display, and processing circuitry configured to receive signals from the catheter, and in response to the signals sample respective voltage values of the signals at respective timing values, and render to the display respective intracardiac electrograms (IEGM) presentation strips representing electrical activity in the tissue that is sensed by the catheter electrodes at the respective locations, each of the IEGM presentation strips including a linear array of respective shapes associated with, and arranged in a temporal order of, respective ones of the timing values, fillers of the respective shapes being formatted responsively to respective ones of the sampled voltage values of a respective one of the signals sampled at respective ones of the timing values.

Further in accordance with an embodiment of the present disclosure the processing circuitry is configured to render to the display the respective IEGM presentation strips, wherein fillers of the respective shapes are at least partially colored responsively to the respective ones of the sampled voltage values of the respective one of the signals sampled at the respective ones of the timing values.

Still further in accordance with an embodiment of the present disclosure the processing circuitry is configured to render to the display the respective IEGM presentation strips, wherein a transparency of the fillers of the respective shapes is adjusted responsively to the respective ones of the sampled voltage values of the respective one of the signals sampled at the respective ones of the timing values.

Additionally, in accordance with an embodiment of the present disclosure the processing circuitry is configured to derive values on an attribute of respective ones of the signals responsively to respective ones of the sampled voltage values and respective ones of the timing values, and render to the display respective IEGM presentation strips, wherein the fillers of the respective shapes are formatted a first formatting responsively to the respective ones of the sampled voltage values of the respective one of the signals sampled at respective ones of the timing values, and the fillers of respective ones of the shapes are also formatted a second formatting responsively to the derived values.

Moreover, in accordance with an embodiment of the present disclosure the attribute is a rate of change of the sampled voltage values.

Further in accordance with an embodiment of the present disclosure the attribute is a fractionation of respective ones of the signals.

Still further in accordance with an embodiment of the present disclosure the first formatting includes color formatting and the second formatting includes transparency formatting.

Additionally, in accordance with an embodiment of the present disclosure the first formatting includes transparency formatting and the second formatting includes color formatting.

Moreover, in accordance with an embodiment of the present disclosure the processing circuitry is configured to render to the display the respective IEGM presentation strips with at least one additional marker selected from any one of the following an alphanumeric symbol, another symbol, a line, a dot, a time annotation, a maximum in current data, a pacing spike.

There is also provided in accordance with another embodiment of the present disclosure, a medical method, including receiving signals from a catheter configured to be inserted into a chamber of a heart of a living subject, and including catheter electrodes configured to contact tissue at respective locations within the chamber of the heart, in response to the signals, sampling respective voltage values of the signals at respective timing values, and rendering to a display respective intracardiac electrograms (IEGM) presentation strips representing electrical activity in the tissue that is sensed by the catheter electrodes at the respective locations, each of the IEGM presentation strips including a linear array of respective shapes associated with, and arranged in a temporal order of, respective ones of the timing values, fillers of the respective shapes being formatted responsively to respective ones of the sampled voltage values of a respective one of the signals sampled at respective ones of the timing values.

Further in accordance with an embodiment of the present disclosure the rendering includes rendering to the display the respective IEGM presentation strips, wherein fillers of the respective shapes are at least partially colored responsively to the respective ones of the sampled voltage values of the respective one of the signals sampled at the respective ones of the timing values.

Still further in accordance with an embodiment of the present disclosure the rendering includes rendering to the display the respective IEGM presentation strips, wherein a transparency of the fillers of the respective shapes is adjusted responsively to the respective ones of the sampled voltage values of the respective one of the signals sampled at the respective ones of the timing values.

Additionally, in accordance with an embodiment of the present disclosure, the method includes deriving values on an attribute of respective ones of the signals responsively to respective ones of the sampled voltage values and respective ones of the timing values, and wherein the rendering includes rendering to the display respective IEGM presentation strips, wherein the fillers of the respective shapes are formatted a first formatting responsively to the respective ones of the sampled voltage values of the respective one of the signals sampled at respective ones of the timing values, and the fillers of respective ones of the shapes are also formatted a second formatting responsively to the derived values.

Moreover, in accordance with an embodiment of the present disclosure the attribute is a rate of change of the sampled voltage values.

Further in accordance with an embodiment of the present disclosure the attribute is a fractionation of respective ones of the signals.

Still further in accordance with an embodiment of the present disclosure the first formatting includes color formatting and the second formatting includes transparency formatting.

Additionally, in accordance with an embodiment of the present disclosure the first formatting includes transparency formatting and the second formatting includes color formatting.

Moreover, in accordance with an embodiment of the present disclosure the rendering includes rendering to the display the respective IEGM presentation strips with at least one additional marker selected from any one of the following an alphanumeric symbol, another symbol, a line, a dot, a time annotation, a maximum in current data, a pacing spike.

There is also provided in accordance with still another embodiment of the present disclosure a software product, including a non-transient computer-readable medium in which program instructions are stored, which instructions, when read by a central processing unit (CPU), cause the CPU to receive signals from a catheter configured to be inserted into a chamber of a heart of a living subject, and including catheter electrodes configured to contact tissue at respective locations within the chamber of the heart, in response to the signals, sample respective voltage values of the signals at respective timing values, and render to a display respective intracardiac electrograms (IEGM) presentation strips representing electrical activity in the tissue that is sensed by the catheter electrodes at the respective locations, each of the IEGM presentation strips including a linear array of respective shapes associated with, and arranged in a temporal order of, respective ones of the timing values, fillers of the respective shapes being formatted responsively to respective ones of the sampled voltage values of a respective one of the signals sampled at respective ones of the timing values.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

As mentioned previously, in a two-step procedure, mapping followed by ablation, electrical activity at points within the heart is typically sensed and measured by advancing a catheter containing one or more electrodes into the heart, and acquiring data at a multiplicity of points. These data are then utilized to select the target areas at which the ablation is to be performed.

In particular, the electrical activity is typically displayed as intracardial electrogram (IEGM) traces for analysis by a physician in order to find sources of arrhythmia. A catheter electrode, which is not in contact with tissue in the heart, generally measures some electrical signal from the heart tissue and a far field signal. When the catheter electrode is in contact with the heart tissue, the voltage value of the signal is mainly based on tissue conductivity, while the far field is minor. Therefore, the physician is generally interested in analyzing the IEGM traces of electrodes in contact with the tissue.

For focal catheters with one or two electrodes, a single IEGM trace is typically displayed for a physician to analyze. A physician can quickly determine based on the form of the signal whether the catheter electrode providing the signal is in contact with the tissue. However, multi-electrode catheters simultaneously capturing electrical activity from different tissue locations may provide data for a plurality of IEGM traces to be displayed at the same time on a single display. In some cases, the number of IEGM traces may be too numerous for the physician to easily determine which of the IEGM traces are provided by electrodes in contact with the tissue, and which are not.

An example of a multielectrode catheter is the Octaray® catheter, with in excess of 48 electrodes, produced by Biosense Webster Inc., of Irvine, Calif., USA. The Octaray includes eight deflectable arms disposed at the distal end of a shaft, with each of the deflectable arms including six electrodes. Some catheters may include more electrodes, for example, but not limited to, 120 electrodes.

In addition to the need to determine electrode contact during mapping discussed above, the physician performing an ablation procedure monitors the contact of electrodes with tissue as effective ablation generally requires sufficient contact between the ablation electrode(s) and the tissue. For small numbers of electrodes, monitoring the contact may be performed by presenting a measure of the contact, such as the impedance seen by an electrode or the force on the electrode, numerically or even graphically. However, as the number of active electrodes used in an ablation procedure increases, it becomes increasingly difficult for the physician to monitor any parameter for the individual electrodes. In the case of electrode contact, this problem is exacerbated by the fact that in most cases as the contact varies, so the parameter measuring the contact also varies.

Embodiments of the present invention solve the above problems during a medical procedure such as a mapping or ablation procedure, by presenting a physician with multi-channel color-formatted IEGM presentation strips instead of showing IEGM traces (graphs of voltage value against time). Each IEGM presentation strip represents a sampling of IEGM voltage values of a signal (detected by a respective catheter electrode) using colored shapes (e.g., rectangles, oblongs, ovals, or any suitable shape) arranged in a linear array in the strip. The shapes are colored according to the sampled voltage values, and arranged in the presentation strip according to a temporal order of respective timing values associated with the sampled voltage values coded in the colored shapes. For example, each successive shape in the strip may correspond with a next timing value at which a sample was taken, and each shape is color-coded according the sampled voltage value sampled at the timing value associated with that shape.

In this way, the color coding of the linear array of shapes in the presentation strip represents the voltage values in a signal detected by a respective catheter electrode.

The presentation strips may be shown one above the other on a display thereby allowing the presentation of many IEGM presentation strips, associated with many catheter electrodes, on a single screen. Salient and other features of the heart electrical activity may be gleaned from the strips such as the voltage values of maxima and minima, spacing of peaks, and the rate of change of the voltage values. For example, the rate of change of voltage is indicated by the width of color bands in the strips. For example, color changes over a single shape represents a quicker rate of change than a color change over several adjacent shapes.

In some embodiments, the shapes may be formatted using another formatting method, for example, using different transparency levels for a filler of the shapes.

Additionally, or alternatively, the shapes of the IEGM presentations strips may be formatted to show another attribute of the signals, such as, a rate of change of the respective signal, or a fractionation of the respective signal. When different attributes of the signals are shown in a single IEGM presentation strip, one attribute may be represented using one formatting type (e.g., using different coloring) and another attribute may be represented using a different formatting type (e.g., using different transparency levels).

In some embodiments. IEGM traces may be optionally displayed in addition to the IEGM presentation strips.

Some embodiments include a medical system, comprising a catheter which is inserted into a chamber of a heart of a living subject. The catheter includes electrodes which contact tissue at respective locations within the chamber of the heart. The medical system may include processing circuitry that receives signals from the catheter, and in response to the signals samples respective voltage values of the signals at respective timing values.

The processing circuitry optionally derives values on an attribute of respective ones of the signals responsively to respective ones of the sampled voltage values and respective ones of the timing values. The attribute may be a rate of change of the sampled voltage values, or a fractionation of respective ones of the signals.

The processing circuitry renders to a display, in response to the signals, respective intracardiac electrograms (IEGM) presentation strips representing electrical activity in the tissue that is sensed by the catheter electrodes at the respective locations. Each IEGM presentation strip includes a linear array of respective shapes associated with, and arranged in a temporal order of, respective ones of the timing values. Fillers of the respective shapes are formatted responsively to respective ones of the sampled voltage values of a respective one of the signals sampled at respective ones of the timing values. In some embodiments, the fillers are formatted based on the sampled voltage values or based on another attribute (e.g., rate of change of voltage value or fractionation) which is based on the sampled voltage values and the timing values. Therefore, the formatting of the IEGM presentation strips may represent the sampled amplitudes, the rate of change of the sampled voltage values, and/or the fractionation.

In some embodiments, the processing circuitry renders to the display the respective IEGM presentation strips with the fillers of the respective shapes being at least partially colored responsively to the respective ones of the sampled voltage values of a respective one of the signals sampled at the respective ones of the timing values. In other embodiments, the processing circuitry renders to the display the respective IEGM presentation strips with a transparency of the fillers of the respective shapes being adjusted responsively to the respective ones of the sampled voltage values of the respective one of the signals sampled at the respective ones of the timing values.

In some embodiments, the processing circuitry renders to the display respective IEGM presentation strips, wherein: the fillers of the respective shapes are formatted according to a first formatting responsively to the respective ones of the sampled voltage values of the respective one of the signals sampled at respective ones of the timing values, and the fillers of respective ones of the shapes are also formatted according to a second formatting responsively to the derived values (e.g. representing another attribute of the signals such as rate of change of voltage value or fractionation). Therefore, at least some of the shapes may be formatted with both the first formatting and the second formatting. For example, at least some of the shapes may be formatted with both color and transparency. The first formatting and second formatting may be selected from any suitable formatting scheme for example, but not limited to, color formatting or transparency formatting. In some embodiments, the first formatting includes color formatting while the second formatting includes transparency formatting. In other embodiments, the first formatting includes transparency formatting and the second formatting includes color formatting.

In some embodiments, the processing circuitry renders to the display the respective IEGM presentation strips with at least one additional marker selected from any one of the following: an alphanumeric symbol, another symbol, a line, a dot, a time annotation, a maximum in current data, and/or a pacing spike, by way of example only.

System Description

Figure 1:
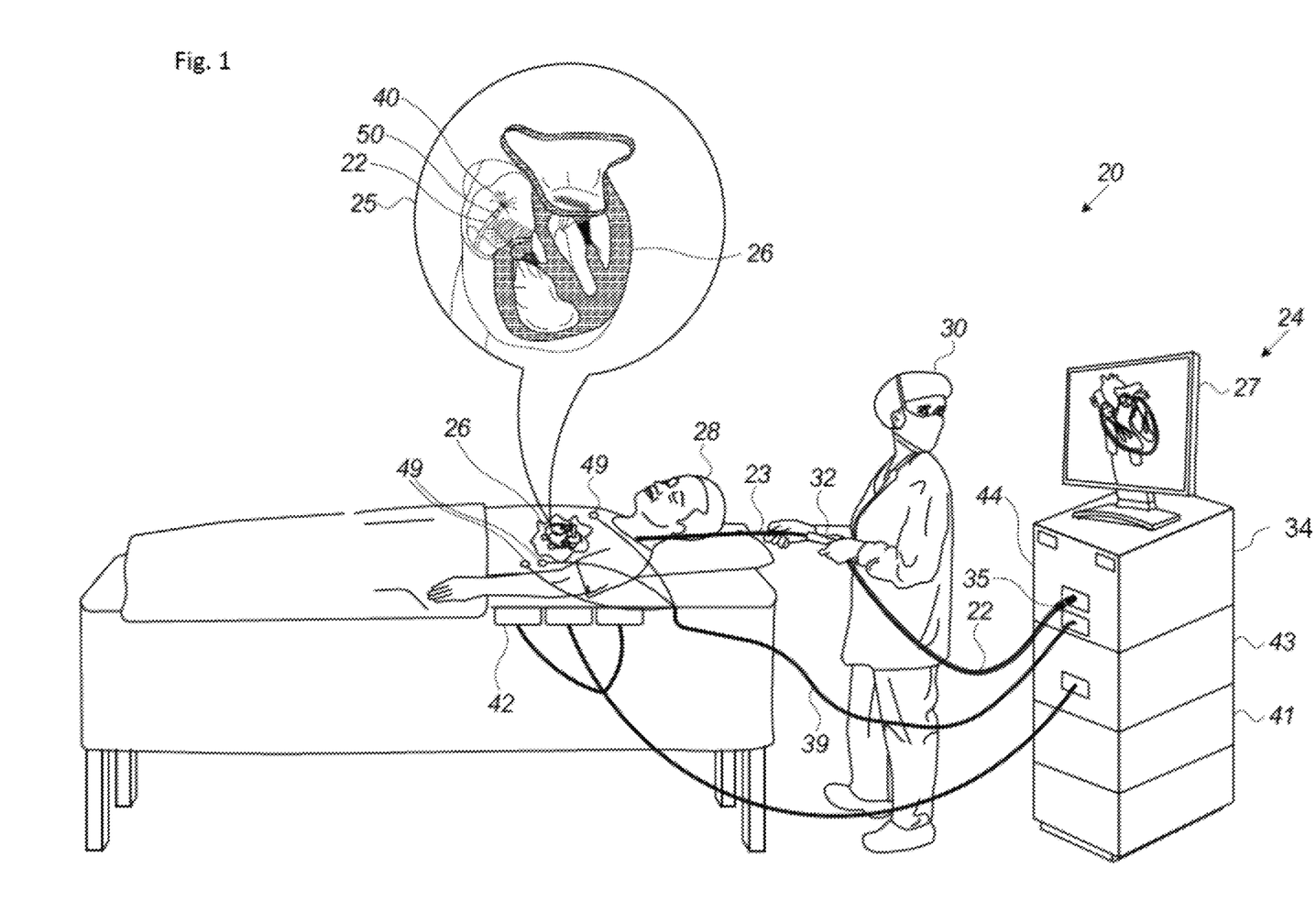
FIG. 1 is a schematic view of a medical procedure system constructed and operative in accordance with an embodiment of the present invention.
Figure 2:
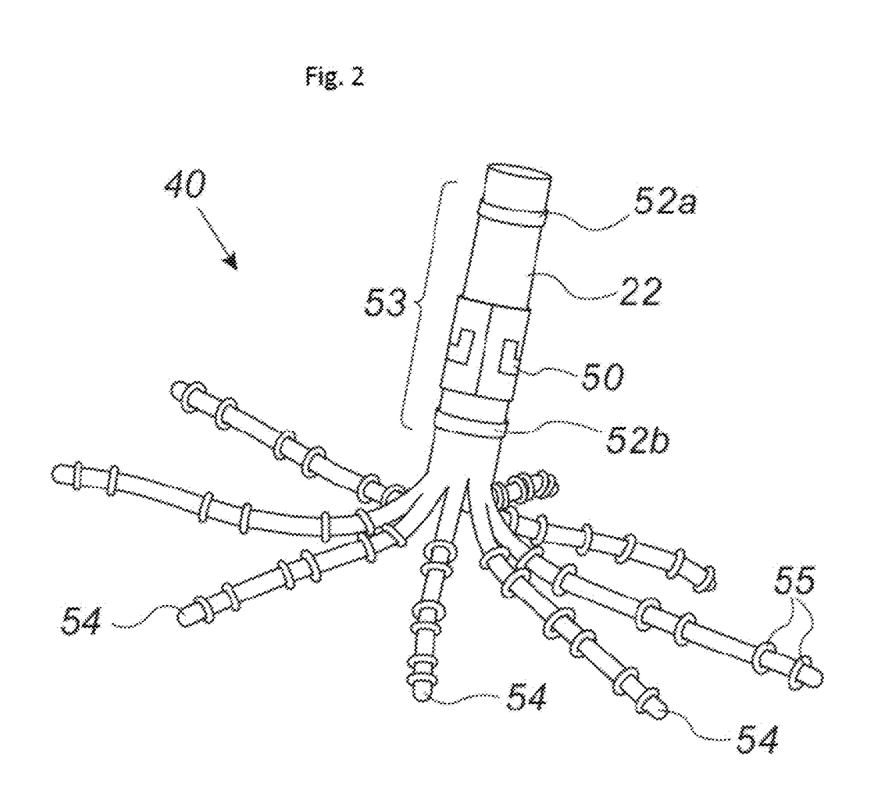
FIG. 2 is a schematic view of a catheter for use in the system of FIG. 1.

Reference is now made to FIG. 1, which is a schematic view of a medical procedure system 20 constructed and operative in accordance with an embodiment of the present invention. Reference is also made to FIG. 2, which is a schematic view of a catheter 40 for use in the system 20 of FIG. 1.

The medical procedure system 20 is used to determine the position of the catheter 40, seen in an inset 25 of FIG. 1 and in more detail in FIG. 2. The catheter 40 includes a shaft 22 and a plurality of deflectable arms 54 (only some labeled for the sake of simplicity) for inserting into a body-part (e.g., a chamber of a heart 26) of a living subject. The deflectable arms 54 have respective proximal ends connected to the distal end of the shaft 22.

The catheter 40 includes a position sensor 53 disposed on the shaft 22 in a predefined spatial relation to the proximal ends of the deflectable arms 54. The position sensor 53 may include a magnetic sensor 50 and/or at least one shaft electrode 52. The magnetic sensor 50 may include at least one coil, for example, but not limited to, a dual-axis or a triple axis coil arrangement to provide position data for location and orientation including roll. The catheter 40 includes multiple catheter electrodes 55 (only some are labeled in FIG. 2 for the sake of simplicity) disposed at different, respective locations along each of the deflectable arms 54. Typically, the catheter 40 may be used for mapping electrical activity in a heart of the living subject using the electrodes 55, or for performing any other suitable function in a body-part of a living subject. The electrodes 55 are configured to contact tissue of the body-part at respective locations with the body part (e.g., within the chamber of the heart).

The medical procedure system 20 may determine a position and orientation of the shaft 22 of the catheter 40 based on signals provided by the magnetic sensor 50 and/or the shaft electrodes 52 (proximal-electrode 52a and distal-electrode 52b) fitted on the shaft 22, on either side of the magnetic sensor 50. The proximal-electrode 52a, the distal-electrode 52b, the magnetic sensor 50 and at least some of the electrodes 55 are connected by wires running through the shaft 22 via a catheter connector 35 to various driver circuitries in a console 24. In some embodiments, at least two of the electrodes 55 of each of the deflectable arms 54, the shaft electrodes 52, and the magnetic sensor 50 are connected to the driver circuitries in the console 24 via the catheter connector 35. In some embodiments, the distal-electrode 52b and/or the proximal electrode 52a may be omitted.

The illustration shown in FIG. 2 is chosen purely for the sake of conceptual clarity. Other configurations of shaft electrodes 52 and electrodes 55 are possible. Additional functionalities may be included in the position sensor 53. Elements which are not relevant to the disclosed embodiments of the invention, such as irrigation ports, are omitted for the sake of clarity.

A physician 30 navigates the catheter 40 to a target location in a body part (e.g., the heart 26) of a patient 28 by manipulating the shaft 22 using a manipulator 32 near the proximal end of the catheter 40 and/or deflection from a sheath 23. The catheter 40 is inserted through the sheath 23, with the deflectable arms 54 gathered together, and only after the catheter 40 is retracted from the sheath 23, the deflectable arms 54 are able to spread and regain their intended functional shape. By containing deflectable arms 54 together, the sheath 23 also serves to minimize vascular trauma on its way to the target location.

Console 24 comprises processing circuitry 41, typically a general-purpose computer and a suitable front end and interface circuits 44 for generating signals in, and/or receiving signals from, body surface electrodes 49 which are attached by wires running through a cable 39 to the chest and to the back, or any other suitable skin surface, of the patient 28.

Console 24 further comprises a magnetic-sensing subsystem. The patient 28 is placed in a magnetic field generated by a pad containing at least one magnetic field radiator 42, which is driven by a unit 43 disposed in the console 24. The magnetic field radiator(s) 42 is configured to transmit alternating magnetic fields into a region where the body-part (e.g., the heart 26) is located. The magnetic fields generated by the magnetic field radiator(s) 42 generate direction signals in the magnetic sensor 50. The magnetic sensor 50 is configured to detect at least part of the transmitted alternating magnetic fields and provide the direction signals as corresponding electrical inputs to the processing circuitry 41.

In some embodiments, the processing circuitry 41 uses the position-signals received from the shaft electrodes 52, the magnetic sensor 50 and the electrodes 55 to estimate a position of the catheter 40 inside an organ, such as inside a cardiac chamber. In some embodiments, the processing circuitry 41 correlates the position signals received from the electrodes 52, 55 with previously acquired magnetic location-calibrated position signals, to estimate the position of the catheter 40 inside a cardiac chamber. The position coordinates of the shaft electrodes 52 and the electrodes 55 may be determined by the processing circuitry 41 based on, among other inputs, measured impedances, or on proportions of currents distribution, between the electrodes 52, 55 and the body surface electrodes 49. The console 24 drives a display 27, which shows the distal end of the catheter 40 inside the heart 26.

The method of position sensing using current distribution measurements and/or external magnetic fields is implemented in various medical applications, for example, in the Carto® system, produced by Biosense Webster Inc. (Irvine, Calif.), and is described in detail in U.S. Pat. Nos. 5,391,199, 6,690,963, 6,484,118, 6,239,724, 6,618,612, 6,332,089, 7,756,576, 7,869,865, and 7,848,787, in PCT Patent Publication WO 96/05768, and in U.S. Patent Application Publications 2002/0065455 A1, 2003/0120150 A1 and 2004/0068178 A1.

The Carto®3 system applies an Active Current Location (ACL) impedance-based position-tracking method. In some embodiments, using the ACL method, the processing circuitry 41 is configured to create a mapping (e.g., current-position matrix (CPM)) between indications of electrical impedance and positions in a magnetic coordinate frame of the magnetic field radiator(s) 42. The processing circuitry 41 estimates the positions of the shaft electrodes 52 and the electrodes 55 by performing a lookup in the CPM.

Processing circuitry 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

FIG. 1 shows only elements related to the disclosed techniques, for the sake of simplicity and clarity. The system 20 typically comprises additional modules and elements that are not directly related to the disclosed techniques, and thus are intentionally omitted from FIG. 1 and from the corresponding description.

The catheter 40 described above includes eight deflectable arms 54 with six electrodes per arm 54. Any suitable catheter may be used instead of the catheter 40, for example, a catheter with a different number of flexible arms and/or electrodes per arm, or a different probe shape such as a balloon catheter, a basket catheter, or a lasso catheter, by way of example only.

The medical procedure system 20 may also perform ablation of heart tissue using any suitable catheter, for example using the catheter 40 or a different catheter and any suitable ablation method. The console 24 may include an RF signal generator 34 configured to generate RF power to be applied by an electrode or electrodes of a catheter connected to the console 24, and one or more of the body surface electrodes 49, to ablate a myocardium of the heart 26. The console 24 may include a pump (not shown), which pumps irrigation fluid into an irrigation channel to a distal end of a catheter performing ablation. The catheter performing the ablation may also include temperature sensors (not shown) which are used to measure a temperature of the myocardium during ablation and regulate an ablation power and/or an irrigation rate of the pumping of the irrigation fluid according to the measured temperature.

Figure 3:
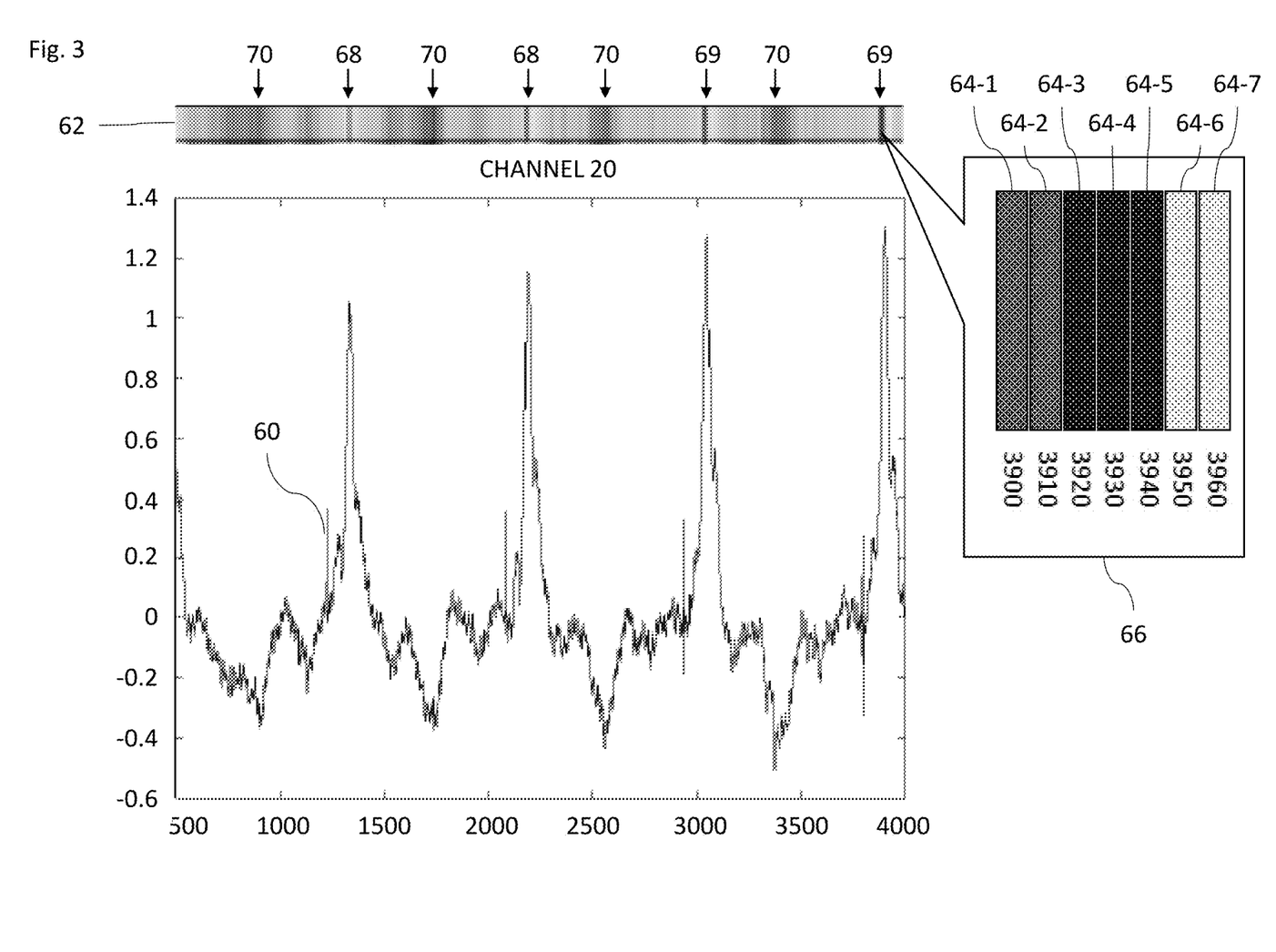
FIG. 3 is a schematic view of an IEGM trace and an IEGM presentation strip, which is produced by the system of FIG. 1.

Reference is now made to FIG. 3, which is a schematic view of an IEGM trace 60 and an IEGM presentation strip 62, which is produced by the system 20 of FIG. 1. The IEGM trace 60 shows the changes in voltage value against time using a line graph for a signal received from one of the electrodes 55 of the catheter 40 (FIG. 2).

To generate the IEGM presentation strip 62, the voltage values of the received signal are sampled at suitable time intervals. The voltage value at a sampled time may be a positive or negative value. The time interval between samples may be any suitable value, for example, but not limited to, in the range of 1 to 50 milliseconds. The voltage values sampled at respective timing values are then converted to color values. The color values may be derived based on looking up color values in a table which maps voltage value ranges to color values. Alternatively, the color values may be computed using a function which receives voltage value as input and outputs a color value. The color values may be defined using a known color model such as RGB or based on a custom color model. Respective shapes 64 of the IEGM presentation strip 62 are assigned with the respective timing values at which the signal was sampled. The respective shapes 64 are then colored according to the respective color values derived from the respective sampled voltage values sampled at the respective timing values.

For example, shapes 64-1 to 64-7, shown in an inset 66, are assigned timing values of 3900, 3910, 3920, 3930, 3940, 3950, and 3960 milliseconds, respectively. The voltages sampled at 3900, 3910, 3920, 3930, 3940, 3950, and 3960 milliseconds from the signal equal to, 1.2, 1.24, 1.3, 1.33, 1.31, 1.15 and 1.1, respectively. Color values corresponding to red, red, dark red, dark red, dark red, orange, and orange are derived from the voltages 1.2, 1.24, 1.3, 1.33, 1.31, 1.15 and 1.1, respectively. The shapes 64-1 to 64-7 are then colored with the colors: red, red, dark red, dark red, dark red, orange, and orange, respectively. It will be noted that two or more different voltages may map to the same color. For example, the voltage of 1.2 and 1.24 both map to red.

The shapes 64 may be selected from any suitable shape such as a rectangle or an oval. The shapes 64 may have any suitable height for example, from 1 to 100 mm, or even higher, depending on the size of the display 27 (FIG. 1) and the number of IEGM presentation strips 62 being displayed at the same time. The shapes 64 may have any suitable width, for example, from a single pixel to 5 mm, depending on the size of the display 27 and the distance of the display from the physician 30 (FIG. 1) and the timing interval between samples.

Although the IEGM presentation strip 62 shown in FIG. 3 is shown in grayscale due to the limitations of patent drawings, the IEGM presentation strip 62 may be displayed on a display using color in which peaks are shown using a red color (arrows 68) and a dark red color (arrows 69), and troughs are shown using a dark blue color (arrows 70), by way of example. Any suitable color coding may be used to represent voltage value with any suitable colors.

Salient and other features of the heart electrical activity may be gleaned from the IEGM presentation strip 62 such as the voltage values of maxima and minima, spacing of peaks, and the rate of change of the voltage values. For example, the rate of change of voltage is indicated by the width of color bands in the strips. For example, color changes over a single shape 64 represents a quicker rate of change than a color change over several adjacent shapes 64.

In some embodiments, the shapes 64 may be formatted using another formatting method (instead of using different colors), for example, using different transparency levels for a filler of the shapes 64. The filler of the shapes 64 may be a solid or patterned filler which has its transparency level adjusted according to the voltage value associated with the shapes.

Figure 4:
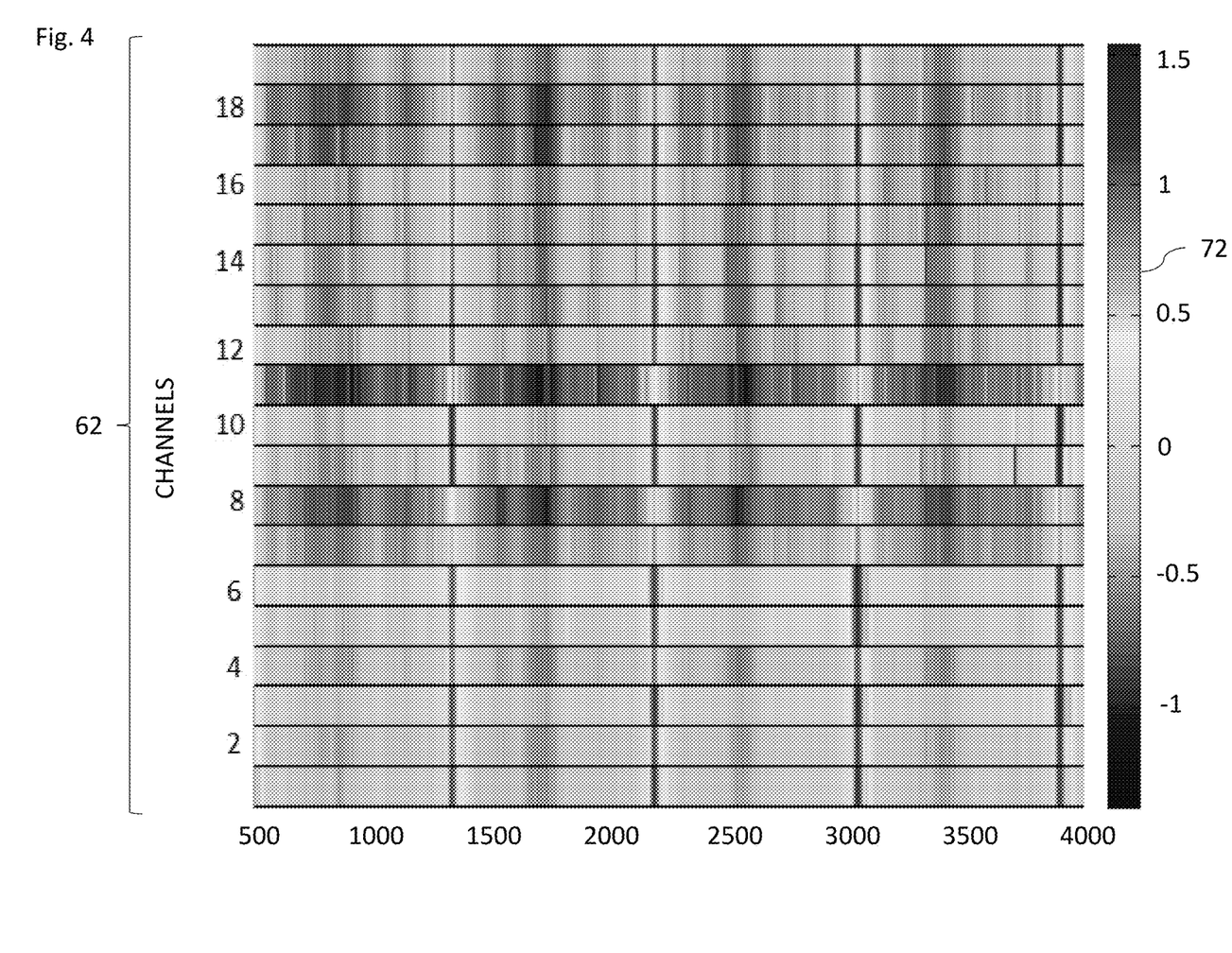
FIG. 4 is a schematic view of multiple IEGM presentation strips.

Reference is now made to FIG. 4, which is a schematic view of multiple IEGM presentation strips 62. The IEGM presentation strips 62 respectively represent signals received from nineteen of the electrodes 55 of the catheter 40 (FIG. 1). The IEGM presentation strips 62 of channels 8, 11, 17, and 18 show more activity in the negative voltage ranges than the IEGM presentation strips 62 of the other channels.

FIG. 4 also shows a legend 72 which provides a lookup for the physician 30 (FIG. 1) between the various colors in the IEGM presentation strips 62 and the corresponding voltage values. The top of the legend may be colored in dark red, and the bottom of the legend in dark blue, by way of example only.

The IEGM presentation strips 62 are shown one above the other on a display thereby allowing the presentation of many IEGM presentation strips 62 on a single display screen.

In some embodiments, the IEGM presentation strips 62 may show other attributes of the signals, such as, a rate of change of the respective signal, or a fractionation of the respective signal, instead of showing the voltage values over time, by formatting the shapes 64 according to values of the other attribute(s).

In other embodiments, the IEGM presentation strip 62 may show other attributes of the signals, such as, a rate of change of the respective signal, or a fractionation of the respective signal, in addition to showing the voltage values over time, by formatting the shapes 64 according to values of the other attribute(s) using one formatting type (e.g., using different transparency levels) and by formatting the shapes 64 according to the voltage values using a different formatting type (e.g., using different coloring).

Figure 5:
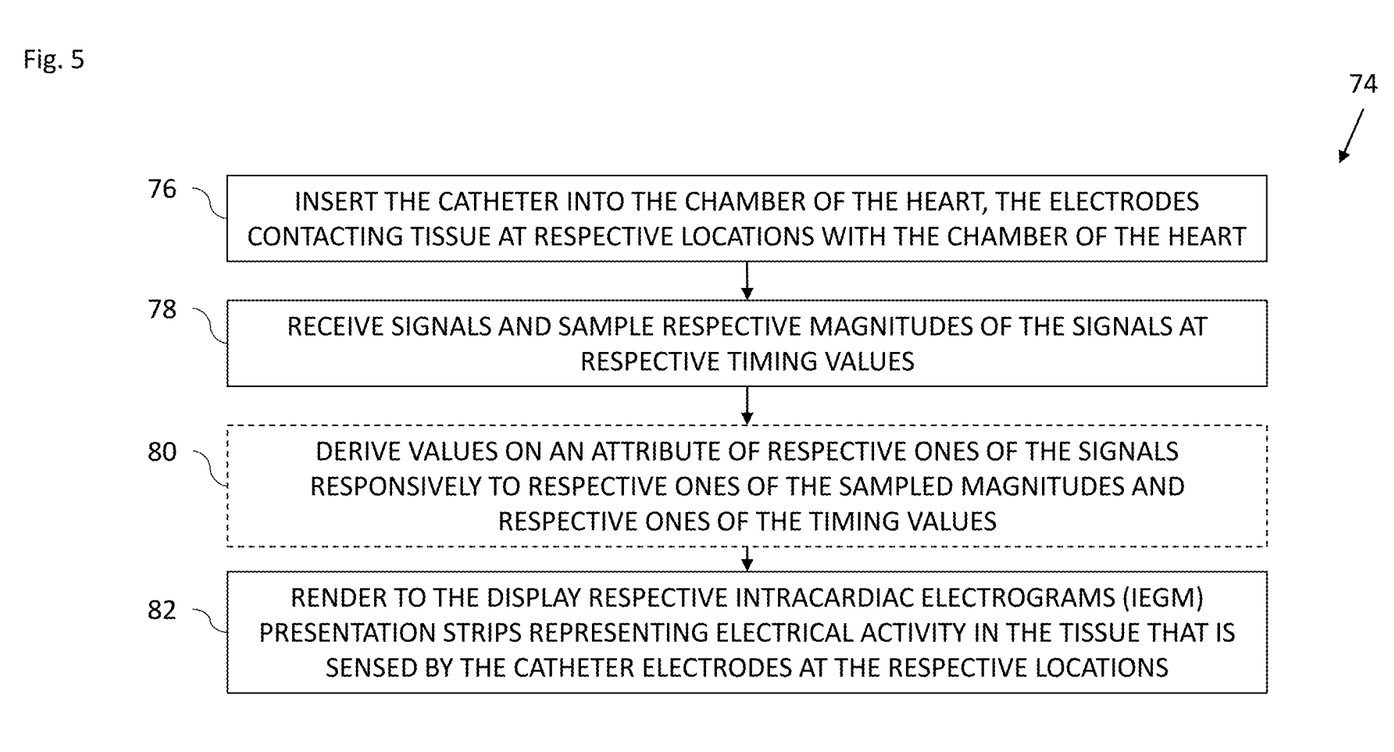
FIG. 5 is a flowchart including steps in a method of operation of the system of FIG. 1.

Reference is now made to FIG. 5, which is a flowchart 74 including steps in a method of operation of the system 20 of FIG. 1.

The catheter 40 (FIG. 1) is configured to be inserted (block 76) into a chamber of the heart 26 (FIG. 1) of a living subject, and includes catheter electrodes 55 (FIG. 2) configured to contact tissue at respective locations within the chamber of the heart 26.

The processing circuitry 41 (FIG. 1) is configured to receive signals from the catheter 40, and in response to the signals sample (block 78) respective voltage values of the signals at respective timing values.

The processing circuitry 41 (FIG. 1) is optionally configured to derive (block 80) values on an attribute of respective ones of the signals responsively to respective ones of the sampled voltage values and respective ones of the timing values. The attribute may be a rate of change of the sampled voltage values, or a fractionation of respective ones of the signals, for example.

The processing circuitry 41 (FIG. 1) is configured to render (block 82) to the display 27 (FIG. 1), in response to the signals, respective intracardiac electrograms (IEGM) presentation strips 62 (FIG. 3) representing electrical activity in the tissue that is sensed by the catheter electrodes 55 at the respective locations. Each IEGM presentation strip 62 includes a linear array of respective shapes 64 (FIG. 3) associated with, and arranged in a temporal order of, respective ones of the timing values. Fillers of the respective shapes 64 are formatted responsively to respective ones of the sampled voltage values of a respective one of the signals sampled at respective ones of the timing values.

The formatting may be according to the sampled voltage values or values based on at least some of the sampled values. For example, the formatting may be based on a rate of change of the sampled voltage values, or a fractionation of respective ones of the signals. Therefore, the IEGM presentation strips 62 may show the rate of change of the sampled voltage values or the fractionation.

In some embodiments, the processing circuitry 41 (FIG. 1) is configured to render to the display 27 (FIG. 1) the respective IEGM presentation strips 62 with fillers of the respective shapes 64 being at least partially colored responsively to the respective ones of the sampled voltage values of the respective one of the signals sampled at the respective ones of the timing values. In other embodiments, the processing circuitry 41 (FIG. 1) is configured to render to the display 27 (FIG. 1) the respective IEGM presentation strips 62 with a transparency of the fillers of the respective shapes 64 being adjusted responsively to the respective ones of the sampled voltage values of the respective one of the signals sampled at the respective ones of the timing values.

In some embodiments, the processing circuitry 41 (FIG. 1) is configured to render to the display 27 (FIG. 1) the respective IEGM presentation strips 62 with the fillers of the respective shapes 64 being formatted according to a first formatting responsively to the respective ones of the sampled voltage values of the respective one of the signals sampled at respective ones of the timing values, and the fillers of respective ones of the shapes 64 also being formatted according to a second formatting responsively to the derived values (derived in the step of block 80). The first formatting and second formatting may be selected from any suitable formatting scheme for example, but not limited to, color formatting or transparency formatting. In some embodiments, the first formatting includes color formatting while the second formatting includes transparency formatting. In other embodiments, the first formatting includes transparency formatting and the second formatting includes color formatting.

In some embodiments, the processing circuitry 41 (FIG. 1) is configured to render to the display 27 (FIG. 1) the respective IEGM presentation strips with at least one additional marker selected from any one of the following: an alphanumeric symbol (e.g., channel numbers of FIG. 4), another symbol (e.g., the legend 72 of FIG. 4), a line (not shown), a dot (not shown), a time annotation (the timing values of FIG. 4), a maximum in current data (not shown), a pacing spike (not shown).

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g. "about 90%" may refer to the range of values from 71% to 99%.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:

1. A medical system, comprising:
a catheter configured to be inserted into a chamber of a heart of a living subject, and including catheter electrodes configured to contact tissue at respective locations within the chamber of the heart;
a display; and
processing circuitry configured to receive signals from the catheter, and in response to the signals:
sample respective voltage values of the signals at respective timing values; and
render to the display respective intracardiac electrograms (IEGM) presentation strips representing electrical activity in the tissue that is sensed by the catheter electrodes at the respective locations, each of the IEGM presentation strips including a linear array of respective shapes associated with, and arranged in a temporal order of, respective ones of the timing values, fillers of the respective shapes being formatted responsively to respective ones of the sampled voltage values of a respective one of the signals sampled at respective ones of the timing values, wherein the shapes of the IEGM presentation strips are formatted to show additional attributes of the signals, including rate of change of the respective signal and a fractionation of the respective signal.

2. The system according to claim 1, wherein the processing circuitry is configured to render to the display the respective IEGM presentation strips, wherein fillers of the respective shapes are at least partially colored responsively to the respective ones of the sampled voltage values of the respective one of the signals sampled at the respective ones of the timing values.

3. The system according to claim 1, wherein the processing circuitry is configured to render to the display the respective IEGM presentation strips, wherein a transparency of the fillers of the respective shapes is adjusted responsively to the respective ones of the sampled voltage values of the respective one of the signals sampled at the respective ones of the timing values.

4. The system according to claim 1, wherein the processing circuitry is configured to:
derive values on an attribute of respective ones of the signals responsively to respective ones of the sampled voltage values and respective ones of the timing values; and
render to the display respective IEGM presentation strips, wherein:
the fillers of the respective shapes are formatted according to a first formatting responsively to the respective ones of the sampled voltage values of the respective one of the signals sampled at respective ones of the timing values, and
the fillers of respective ones of the shapes are also formatted according to a second formatting responsively to the derived values.

5. The system according to claim 4, wherein the attribute is a rate of change of the sampled voltage values.

6. The system according to claim 4, wherein the attribute is a fractionation of respective ones of the signals.

7. The system according to claim 4, wherein the first formatting includes color formatting and the second formatting includes transparency formatting.

8. The system according to claim 4, wherein the first formatting includes transparency formatting and the second formatting includes color formatting.

9. The system according to claim 1, wherein the processing circuitry is configured to render to the display the respective IEGM presentation strips with at least one additional marker selected from any one of the following: an alphanumeric symbol, another symbol, a line, a dot, a time annotation, a maximum in current data, a pacing spike.

10. A medical method, comprising:
receiving signals from a catheter configured to be inserted into a chamber of a heart of a living subject, and including catheter electrodes configured to contact tissue at respective locations within the chamber of the heart;
in response to the signals, sampling respective voltage values of the signals at respective timing values; and
rendering to a display respective intracardiac electrograms (IEGM) presentation strips representing electrical activity in the tissue that is sensed by the catheter electrodes at the respective locations, each of the IEGM presentation strips including a linear array of respective shapes associated with, and arranged in a temporal order of, respective ones of the timing values, fillers of the respective shapes being formatted responsively to respective ones of the sampled voltage values of a respective one of the signals sampled at respective ones of the timing values, wherein the shapes of the IEGM presentation strips are formatted to show additional attributes of the signals, including rate of change of the respective signal and a fractionation of the respective signal.

11. The method according to claim 10, wherein the rendering comprises rendering to the display the respective IEGM presentation strips, wherein fillers of the respective shapes are at least partially colored responsively to the respective ones of the sampled voltage values of the respective one of the signals sampled at the respective ones of the timing values.

12. The method according to claim 10, wherein the rendering comprises rendering to the display the respective IEGM presentation strips, wherein a transparency of the fillers of the respective shapes is adjusted responsively to the respective ones of the sampled voltage values of the respective one of the signals sampled at the respective ones of the timing values.

13. The method according to claim 10, further comprising deriving values on an attribute of respective ones of the signals responsively to respective ones of the sampled voltage values and respective ones of the timing values, and wherein the rendering comprises rendering to the display respective IEGM presentation strips, wherein: the fillers of the respective shapes are formatted according to a first formatting responsively to the respective ones of the sampled voltage values of the respective one of the signals sampled at respective ones of the timing values, and the fillers of respective ones of the shapes are also formatted according to a second formatting responsively to the derived values.

14. The method according to claim 13, wherein the attribute is a rate of change of the sampled voltage values.

15. The method according to claim 13, wherein the attribute is a fractionation of respective ones of the signals.

16. The method according to claim 13, wherein the first formatting includes color formatting and the second formatting includes transparency formatting.

17. The method according to claim 13, wherein the first formatting includes transparency formatting and the second formatting includes color formatting.

18. The method according to claim 10, wherein the rendering comprises rendering to the display the respective IEGM presentation strips with at least one additional marker selected from any one of the following: an alphanumeric symbol, another symbol, a line, a dot, a time annotation, a maximum in current data, a pacing spike.

19. A software product, comprising a non-transient computer-readable medium in which program instructions are stored, which instructions, when read by a central processing unit (CPU), cause the CPU to:
receive signals from a catheter configured to be inserted into a chamber of a heart of a living subject, and including catheter electrodes configured to contact tissue at respective locations within the chamber of the heart;
in response to the signals, sample respective voltage values of the signals at respective timing values; and
render to a display respective intracardiac electrograms (IEGM) presentation strips representing electrical activity in the tissue that is sensed by the catheter electrodes at the respective locations, each of the IEGM presentation strips including a linear array of respective shapes associated with, and arranged in a temporal order of, respective ones of the timing values, fillers of the respective shapes being formatted responsively to respective ones of the sampled voltage values of a respective one of the signals sampled at respective ones of the timing values, wherein the shapes of the IEGM presentation strips are formatted to show additional attributes of the signals, including rate of change of the respective signal and a fractionation of the respective signal.

\* \* \* \* \*